US007952641B2

(12) United States Patent
Narayanaswami et al.

(10) Patent No.: US 7,952,641 B2
(45) Date of Patent: May 31, 2011

(54) SENSOR FOR IMAGING INSIDE EQUIPMENT

(75) Inventors: Chandrasekhar Narayanaswami, Wilton, CT (US); Mandayam Thonadur Raghunath, Bangalore (IN); Ramon Caceres, New York, NY (US); Stefan Berger, New York, NY (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 12/330,443

(22) Filed: Dec. 8, 2008

(65) Prior Publication Data

US 2009/0079827 A1    Mar. 26, 2009

Related U.S. Application Data

(62) Division of application No. 10/874,022, filed on Jun. 22, 2004, now Pat. No. 7,502,068.

(51) Int. Cl.
*H04N 5/225* (2006.01)
*H04N 7/18* (2006.01)
*H04N 9/47* (2006.01)
*G03B 17/00* (2006.01)

(52) U.S. Cl. ............ 348/373; 348/82; 348/86; 348/125; 348/143; 396/427

(58) Field of Classification Search .................... 348/82, 348/83, 86, 90, 92, 125, 126, 143, 151, 158, 348/159, 207.1, 211.8, 211.14, 373; 396/427; 378/57, 58
See application file for complete search history.

(56) References Cited

U.S. PATENT DOCUMENTS

| RE37,709 E | * | 5/2002 | Dukek | ........................ 348/148 |
| 6,614,872 B2 | * | 9/2003 | Bueno et al. | ................... 378/58 |
| 2002/0100053 A1 | * | 7/2002 | Nguyen et al. | ............... 725/105 |
| 2003/0214581 A1 | * | 11/2003 | Ikami | ............................ 348/86 |
| 2004/0016271 A1 | * | 1/2004 | Shah et al. | ...................... 70/159 |
| 2006/0119704 A1 | * | 6/2006 | Buchheit | ...................... 348/143 |
| 2008/0129459 A1 | * | 6/2008 | Bailly et al. | ................. 340/10.1 |

FOREIGN PATENT DOCUMENTS

JP     2005157706 A  *  6/2005
* cited by examiner

*Primary Examiner* — John M Villecco
(74) *Attorney, Agent, or Firm* — Michael J. Buchenhorner; Vazken Alexanian

(57) ABSTRACT

A system for monitoring performance of a machine for detection of visible signs of failure, the system including: a machine enclosure housing a plurality of machine parts; a visual conduit for providing a view of an interior of the machine; an interface to the machine configured to receive images from the visual conduit; and a repair network for linking the interface to a monitoring center that provides for the repair of problems with the machine.

8 Claims, 4 Drawing Sheets

SENSOR FOR IMAGING INSIDE EQUIPMENT

CROSS-REFERENCE TO RELATED APPLICATIONS

This application is a division of, and claims priority from, commonly-owned, co-pending U.S. application Ser. No. 10/874,022, filed on Jun. 22, 2004.

STATEMENT REGARDING FEDERALLY SPONSORED-RESEARCH OR DEVELOPMENT

None.

INCORPORATION BY REFERENCE OF MATERIAL SUBMITTED ON A COMPACT DISC

None.

FIELD OF THE INVENTION

The invention disclosed broadly relates to the field of machines and more particularly relates to the field of diagnosis of problems in machines.

BACKGROUND OF THE INVENTION

When a machine breaks down, it may be difficult and expensive to repair because disassembly may be required to diagnose the problem. There is also a frequent delay in obtaining parts to replace those broken once the problem has been diagnosed. The resulting down time is also a problem.

Remote monitoring of equipment needs different kind of sensors. Common sensors today include temperature sensors, weight sensors, position sensors, etc. The data from these sensors can be remotely viewed to diagnose the condition of the system. However, there are still situations where these sensors are not adequate to diagnose the problem and is necessary for a human being to open up the equipment and look at it. This process is time consuming and there needs to be a better way. The idea is to use imaging inside the equipment to handle situations that cannot be addressed by the above means.

SUMMARY OF THE INVENTION

Briefly, according to the invention, a machine comprises an enclosure; a plurality of parts within the enclosure; and a visual conduit for providing a view inside of the enclosure for detection of visible signs of failure of the machine. The concept of a visual conduit encompasses a broad variety of devices including cameras inside the enclosure that provide images of the interior of the enclosure and alternatively selective transparency or translucence of the enclosure relative to at least some of the parts of the machine housed within the enclosure.

According to another embodiment of the invention a method for designing a machine comprises the steps of: selecting a first material for an enclosure; and selecting a second material for one or more parts within the enclosure; wherein the selection of the materials permits viewing of the parts under certain conditions.

According to another embodiment of the invention a system comprises an interface for receiving images from remote devices; one or more central servers for storing the images for further analysis using image processing techniques; and a transmitter for further distribution of the images to other destinations.

BRIEF DESCRIPTION OF THE DRAWINGS

To describe the foregoing and other exemplary purposes, aspects, and advantages, we use the following detailed description of an exemplary embodiment of the invention with reference to the drawings, in which.

Figure 1:
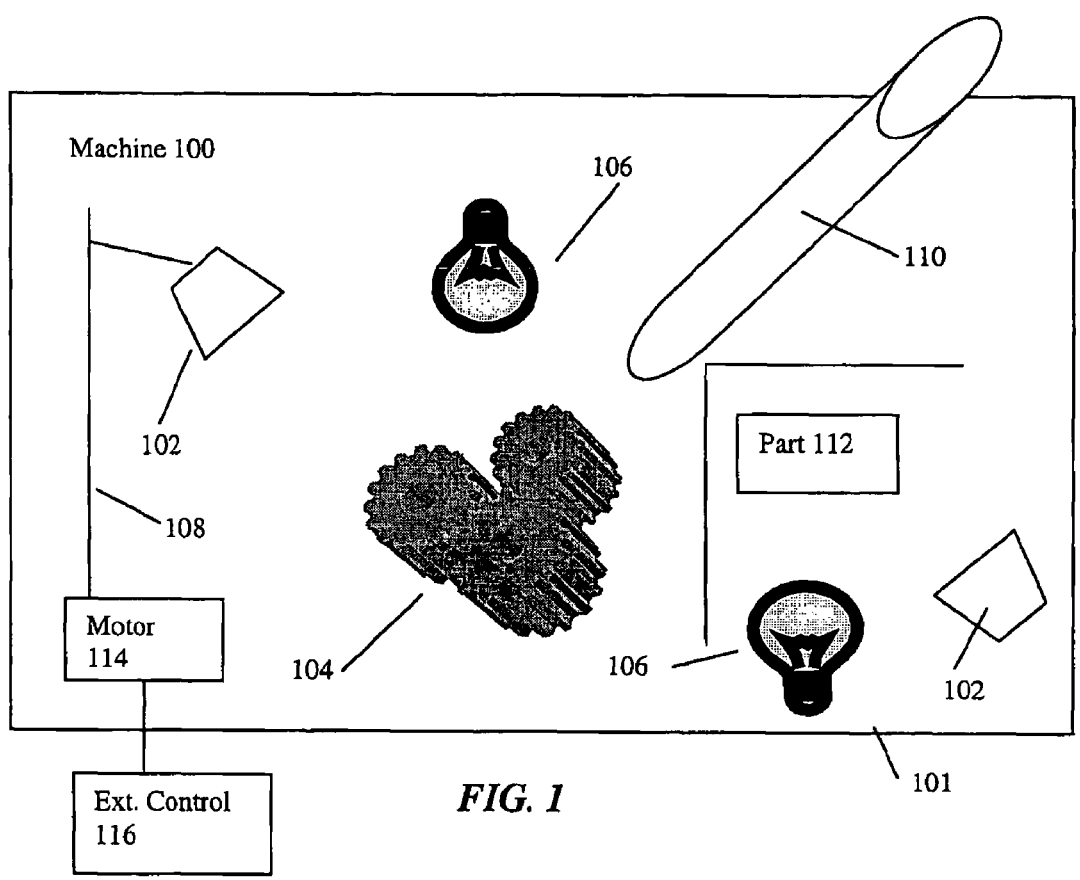
FIG. 1 shows a machine with sensors according to the invention.

While the invention as claimed can be modified into alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents and alternatives falling within the scope of the present invention.

DETAILED DESCRIPTION

FIG. 1 shows a highly-simplified depiction of a machine 100 with sensors according to the invention. The machine 100 comprises an enclosure or housing 101 for machinery 104. In this embodiment, the sensors comprise a set of cameras 102, all located within the machine enclosure 101 to capture images of the machinery 104. Assume that the machine 100 is an expensive piece of equipment such as a printer, magnetic resonance imaging device or the like. In this case a set of parts 104 is malfunctioning. The camera 102 is used to diagnose the problem. In this case assume that the machinery 104 comprises mechanical moving parts and failures can be easily detected by obtaining images of the parts 104 by means of the camera 102 using the light 106 to illuminate the parts. Because the enclosure of the machine need not be opened during a diagnosis operation, the machine can continue to operate showing the cause of failure. Assume that the machine parts 104 are a set of gears and one of the gears is missing a cog. The images produced by the camera 102 are provided to a user outside the machine who can easily determine the cause of the failure. As will be appreciated, the light source 106 may not be required where the camera 102 obtains images using infrared radiation produced by the parts 104 when they are hot as a result of their operation.

The camera 102 can be a still or preferably a video camera with flash, zoom, and other such features. It is preferably controlled by external controls 116. The camera 102 can be mounted on a track 108 and coupled to a motor 114 that is controlled by the external controls 116. The user is presented with the images provided by the camera 102 and can thus interactively control the orientation and movements of the camera to provide the desired images of the machine parts 104.

The camera 102 has a unique identifier (ID) and a wired or wireless link to the outside world for communication with a user. The unique identifier is transmitted to the outside world so that each machine can be identified from other nodes in the network. Alternatively, the camera 102 may be programmed to move automatically providing a set of images that may be stored and later viewed on demand to determine what caused a failure in the past. The light 106 can also be programmed to move automatically or can be moved manually by means of the external control apparatus 116.

An alternative image conduit is provided by a tube 110 having an internally reflective surface (preferably fiber optics) that transmits an image or images of the interior of the machine 100 to the outside. Such a tube 110 can include a camera and light as well. The tube is preferably flexible so that it can negotiate winding paths throughout the machine 100.

The cameras can be placed in locations where even highly obscured parts (such as part 112) can be imaged.

Figure 2:
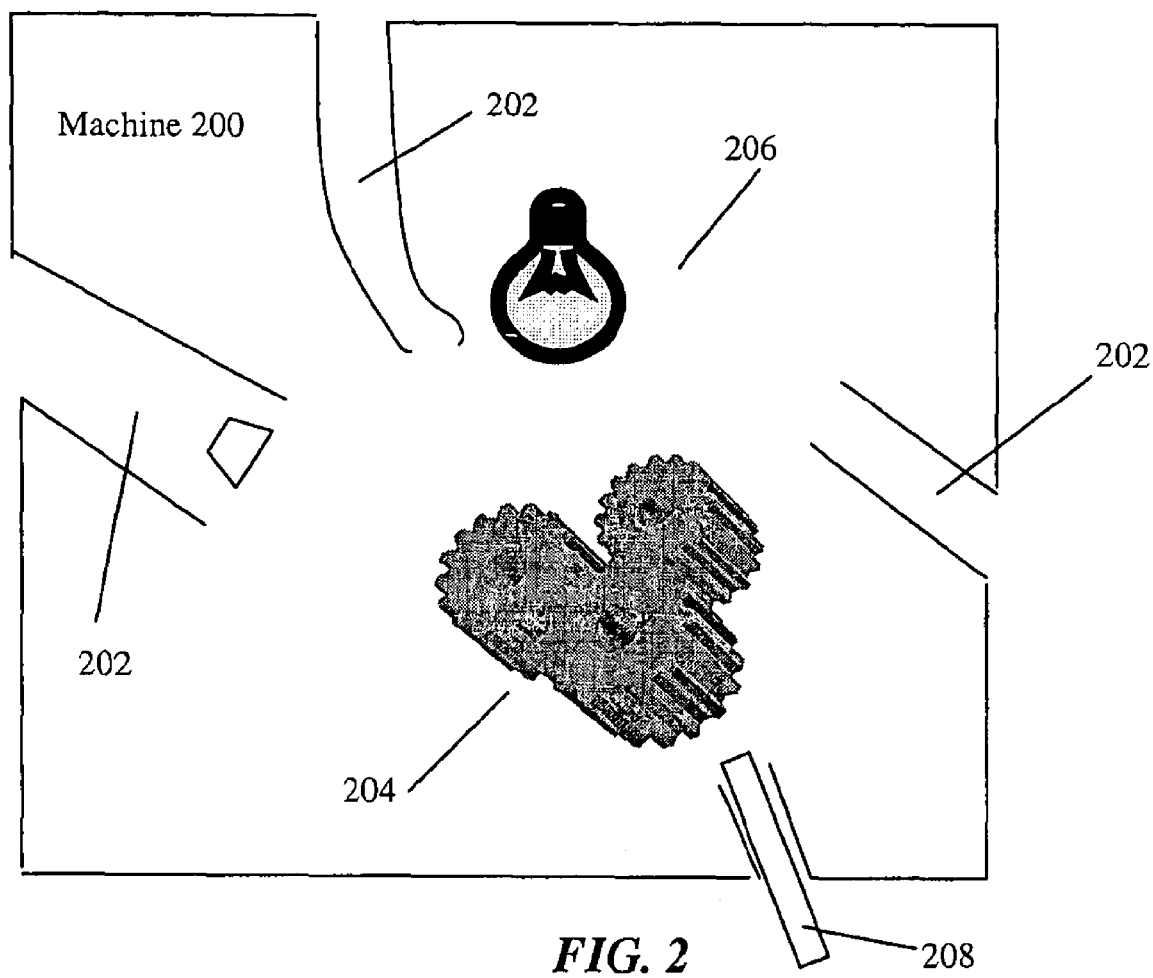
FIG. 2 shows a highly-simplified depiction of a machine according to another embodiment of the invention.

Referring now to FIG. 2, there is shown a machine 200 according to another embodiment of the invention. In this embodiment, the visual conduit comprises a plurality of pathways or canals 202 that are provided throughout the machine to provide images of its interior. As in the case depicted in FIG. 1, a canal 202 provides an image of the machine parts 204 to its users to assist in determining whether the parts are operating properly. A light source 206 provides illumination where necessary. Optional camera guide rails or paths 208 are provided in one of the canals 202 to allow for movement of a camera (not shown) to locations required for providing the desired images. Thus, a camera can be sent through the pathways 208 for providing images throughout the inside of the machine.

Figure 3:
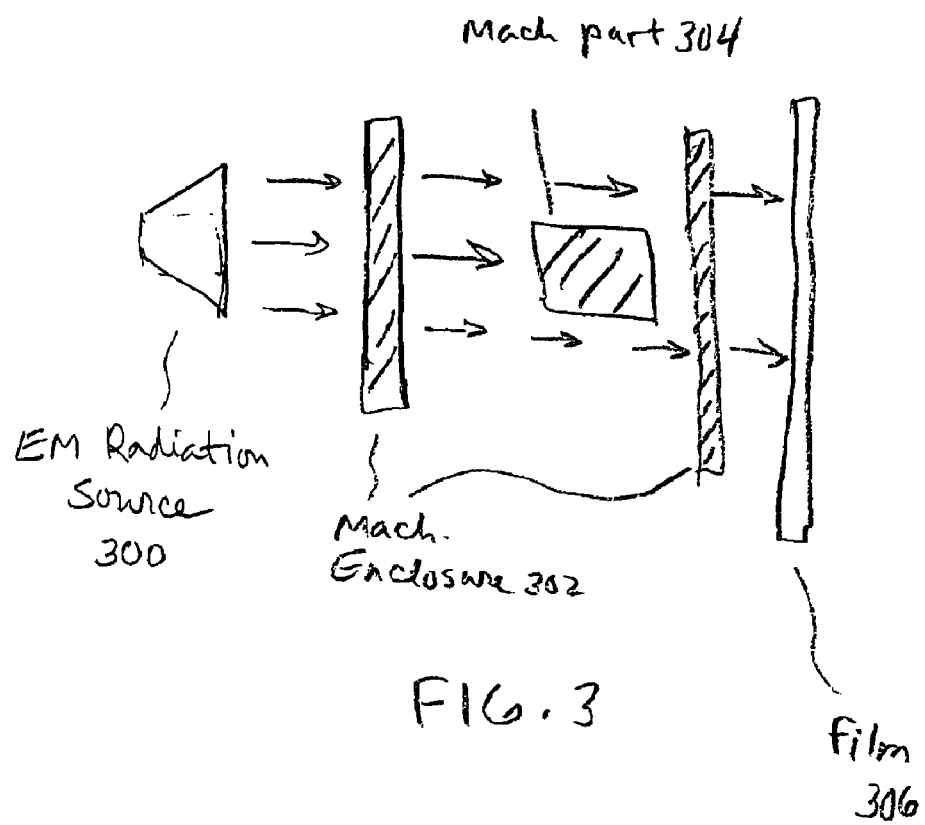
FIG. 3 shows a cross-section of a machine with parts made form materials with different properties.

Referring to FIG. 3, there is shown another embodiment of the invention wherein the visual conduit comprises a machine enclosure 302 made from a material that is transparent to a source of electromagnetic radiation (EMR) 300 at one or more frequencies such as x-ray frequencies. Thus the radiation source 300 provides x-rays that pass through the enclosure 302 relatively unimpeded but are substantially blocked by a machine part 304 that is made from a different material that is opaque to the EMR. The result is an image of the machine part 304 that can be captured at a sensor 306 outside the enclosure 302. An example of a sensor is a film that is sensitive to x-rays. The sensor can be located inside the enclosure 302 and connected to the outside by a communication link to provide the images acquired. The film 306 can be optionally replaced by a sensor (such as charge-coupled devices) that detects the EMR that passes through enclosure 302, and provides the image to the world outside the enclosure.

Figure 4:
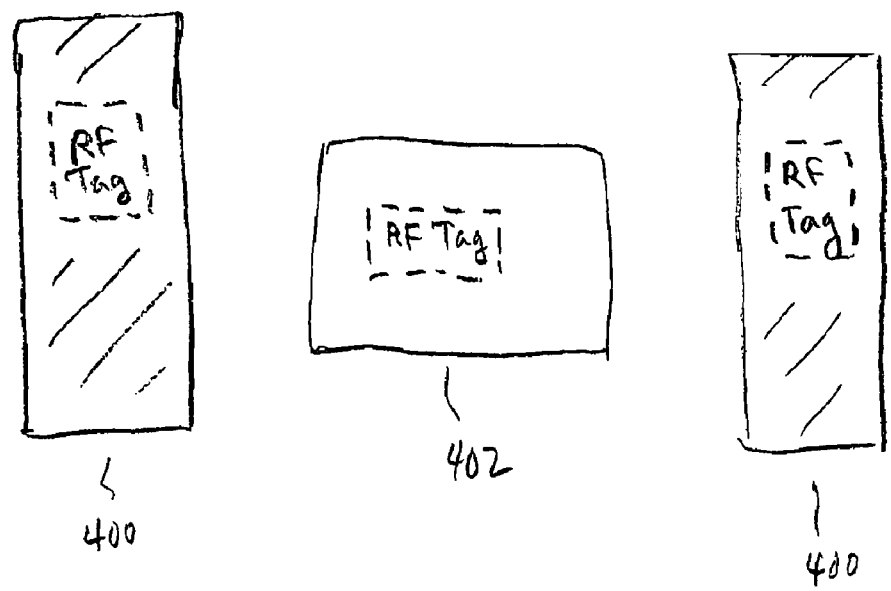
FIG. 4 shows a machine with parts made form materials with different properties wherein RF-tags are embedded in the parts to identify the materials.

Referring to FIG. 4, there is shown another embodiment of the invention wherein the machine enclosure 400 is made from a different material than the interior parts 402 and radio-frequency tags are embedded in the parts to provide an indication of the material from which they are made. An RF-tag reader (not shown) can be used from outside the enclosure 402 to read the information stored in the RF-tag. This provides user information that can be used to determine the properties of the materials so that the user can select an appropriate visualization tool (e.g. x-rays).

Figure 5:
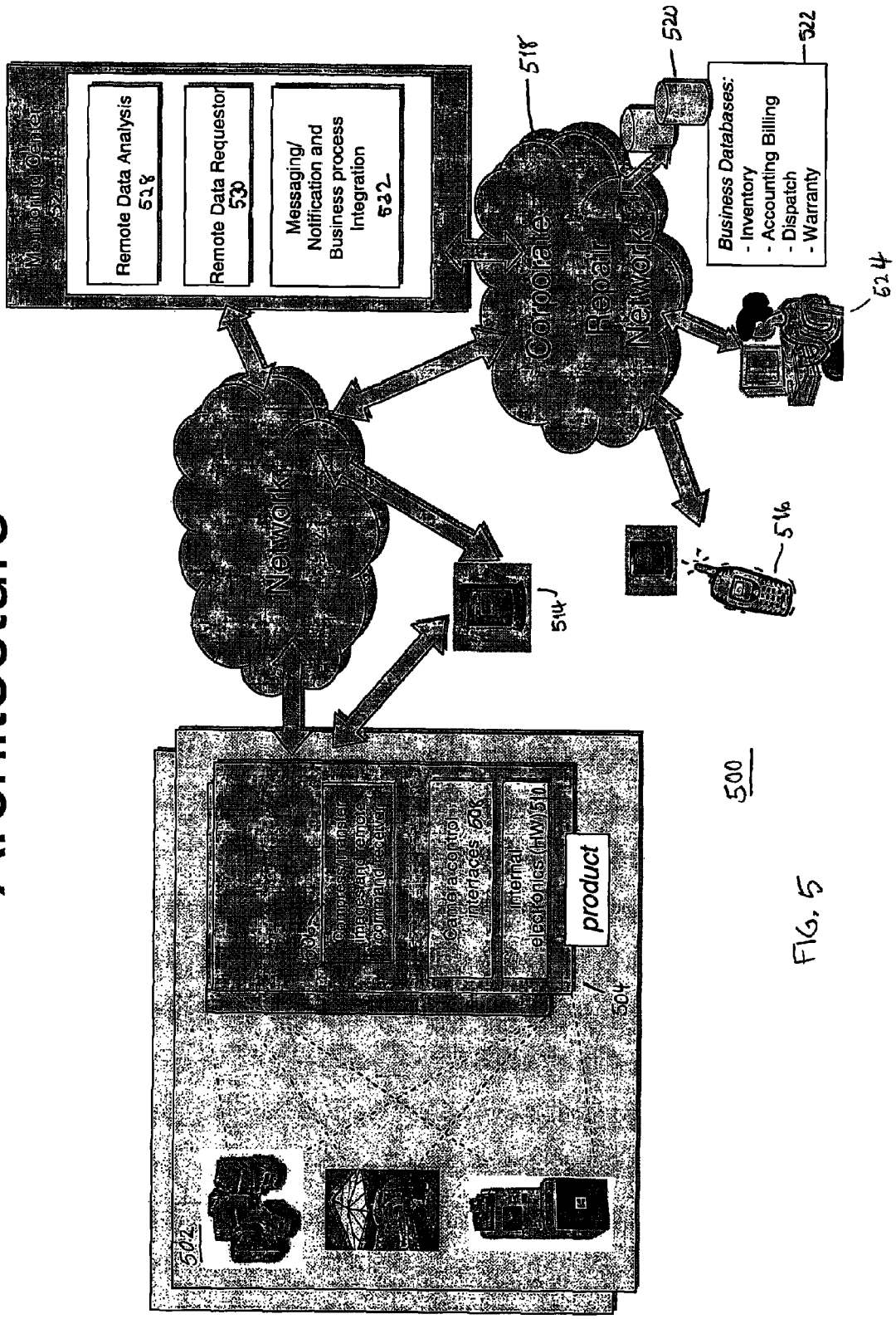
FIG. 5 shows system architecture according to the present invention.

FIG. 5 shows system architecture 500 of a system that uses the invention to diagnose problems in machines. The system 500 monitors a set of equipment 502 for purposes of maintaining its operation. The equipment 502 comprises machines having parts within their interiors that are monitored by means of visual conduits as discussed above. The equipment 502 is typically expensive to repair because of the troubleshooting required. Each item of equipment 502 interfaces with a network 512 by means of an interface 504. The interface 504 comprises a module 506 for compressing/transferring images and receiving remote commands. A module 508 comprises camera control interfaces for controlling the location and orientation of the cameras located inside the equipment and a module 510 comprising the internal electronics for controlling the operation of the visual conduits.

The interface 504 is linked, via a wireless link, with a personal digital assistant 514; and via the network 512 to a monitoring center 526. The monitoring center 526 includes: a remote data analysis module 528; a remote data requester 530; and a messaging/notification and business process integration module 532. The remote data analysis module 528 receives data originating from the monitored machine 502 and transmits the data to a corporate repair network 518. From there, the data can be stored in persistent storage 520, in proprietary business databases 522, downloaded to mobile devices 516 such as cell phones, or downloaded directly to the systems of users 524 who monitor the performance of the machines 502. The remote data requester 530 can be used by a user to request data gathered by sensors monitoring the machines.

The messaging/notification and business process integration module 532 is used to coordinate the tasks performed using various enterprise business applications that may not have compatible syntax or data structures. Module 532 can comprise software such as IBM's WebSphere Business Integration™ software or MQ Series.

What has been shown and discussed is a highly-simplified depiction of a programmable computer apparatus. Those skilled in the art will appreciate that other low-level components and connections are required in any practical application of a computer apparatus.

Therefore, while there has been described what is presently considered to be the preferred embodiment, it will be understood by those skilled in the art that other modifications can be made within the spirit of the invention.

We claim:

1. A method for diagnosing a machine comprising an enclosure and one or more parts inside the enclosure, the method comprising steps of:
    using a radiation source for transmitting electromagnetic radiation at the enclosure at a frequency that penetrates the enclosure and at which the one or more parts inside the enclosure are opaque;
    wherein the machine enclosure is made from a first material that is transparent to the electromagnetic radiation at the frequency;
    wherein the one or more parts inside the enclosure are made from a second material that is not transparent to the electromagnetic radiation at the frequency; and
    using a sensor configured to capture an image of the machine part, said sensor located inside the machine enclosure.

2. The method of claim 1 further comprising:
    using an interface for capturing images from an interior of the enclosure.

3. The method of claim 2 further comprising:
    linking the interface to a monitoring center that provides for repair of problems with the machine.

4. A system for imaging inside a machine enclosure, said system comprising:
    the machine enclosure made from a first material that is transparent to electromagnetic radiation at an at least one frequency;

a machine part located within the machine enclosure, said machine part made from a second material that is opaque to electromagnetic radiation at the at least one frequency;

a sensor for capturing an image of the machine part, said sensor located inside the machine enclosure; and a communication link operatively coupled with the sensor, said communication link connecting said sensor to equipment outside the machine enclosure.

5. The system of claim 4 further comprising a source of the electromagnetic radiation.

6. A method of imaging inside a machine enclosure, said method comprising:

transmitting electromagnetic radiation at the machine enclosure at a frequency that penetrates said machine enclosure and at which at least one machine part located inside said machine enclosure is opaque;

wherein the machine enclosure is made from a first material that is transparent to the electromagnetic radiation at the frequency;

wherein the at least one machine part is made from a second material, said second material being opaque to the electromagnetic radiation;

capturing an image of the machine parts with a sensor located inside the machine enclosure; and connecting the sensor to equipment outside the machine enclosure with a communication link operatively coupled with said sensor.

7. The method of claim 6 further comprising:

using an interface for capturing images from inside the machine enclosure.

8. The method of claim 6 further comprising:

linking the interface to a monitoring center that provides for repair of problems with the at least one machine part.

* * * * *